United States Patent [19]
Jinotti

[11] Patent Number: 5,088,486
[45] Date of Patent: Feb. 18, 1992

[54] CLOSED SYSTEM REUSABLE DUAL PURPOSE CATHETER

[76] Inventor: Walter J. Jinotti, 10 Scott St., New Brunswick, N.J. 08902

[21] Appl. No.: 507,494

[22] Filed: Apr. 11, 1990

[51] Int. Cl.$^5$ .................. A61M 16/00; A61M 25/00; A62B 9/06
[52] U.S. Cl. .................. 128/207.14; 128/200.26; 128/205.12; 128/DIG. 26; 128/911; 128/912; 604/905
[58] Field of Search .............. 128/207.14, 207.15, 128/207.16, 207.17, 205.19, 205.12, 200.24, 200.26; 604/96–905, 43, 45, 118, 119, 171, 192, 173, 200, 263, 267, 268, 284

[56] References Cited

U.S. PATENT DOCUMENTS

| | | | |
|---|---|---|---|
| 3,991,762 | 11/1976 | Radford | 128/207.16 |
| 4,193,406 | 3/1980 | Jinotti | 128/204.18 |
| 4,354,490 | 10/1982 | Rogers | 604/905 |
| 4,416,273 | 11/1983 | Grimes | 128/207.16 |
| 4,432,759 | 2/1984 | Gross et al. | 604/905 |
| 4,517,979 | 5/1985 | Pecenka | 604/96 |
| 4,545,367 | 10/1985 | Tucci | 604/96 |
| 4,551,146 | 11/1985 | Rogers | 604/905 |
| 4,585,440 | 4/1986 | Tchervenkov et al. | 604/267 |
| 4,610,469 | 9/1986 | Wolff-Mooij | 604/905 |
| 4,655,762 | 4/1987 | Rogers | 604/905 |
| 4,810,241 | 3/1989 | Rogers | 604/905 |
| 4,935,010 | 6/1990 | Cox et al. | 604/905 |
| 4,995,386 | 2/1991 | Ng | 128/205.19 |
| 4,995,387 | 2/1991 | Jinotti | 128/205.24 |

*Primary Examiner*—Edgar S. Burr
*Assistant Examiner*—Kimberly L. Asher
*Attorney, Agent, or Firm*—Robert A. Green

[57] ABSTRACT

A dual-purpose catheter for performing suction or oxygen feed on a patient including two cylindrical bodies rotatably coupled together and held together by a spring which is biased to hold the bodies in a first position with respect to each other but permits rotation to a second position. One body includes first and second tubes which can be coupled to a source of suction or a source of oxygen, and the other body includes means for receiving said tubes in a tight fit and tube means for coupling either suction or oxygen to the patient, depending on the rotation state of the two bodies with respect to each other. The catheter bodies include solid tubes positioned to block the oxygen path to the patient when suction is operating and to block the suction path to the patient when oxygen is operating.

20 Claims, 4 Drawing Sheets

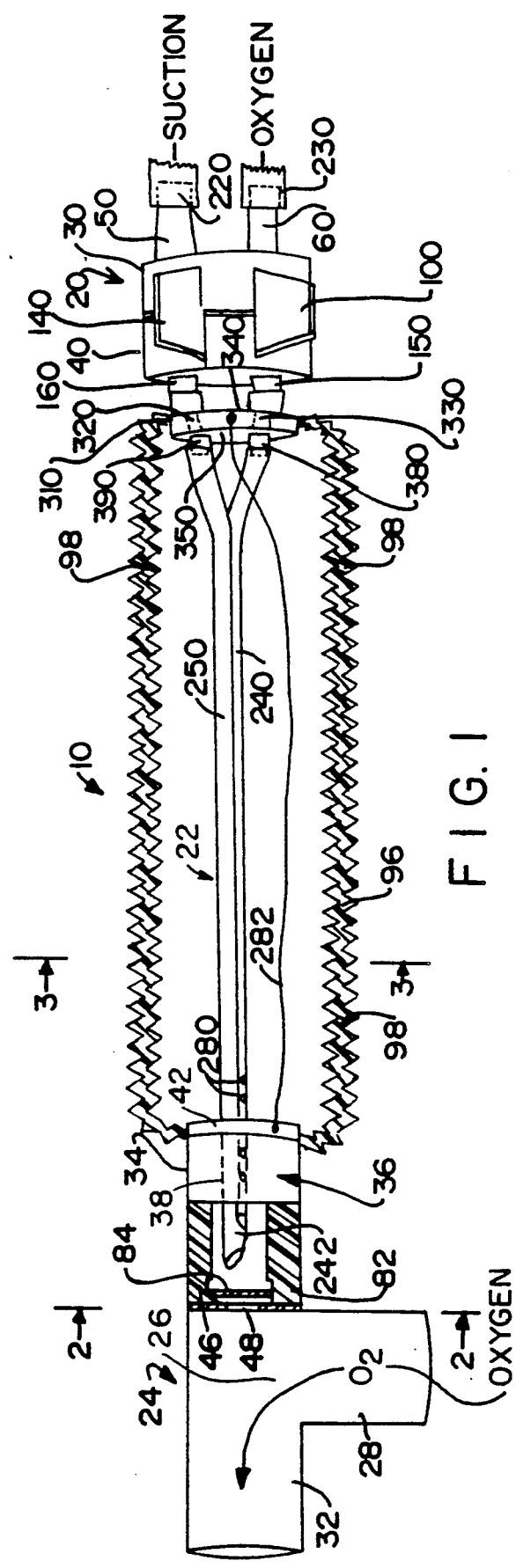
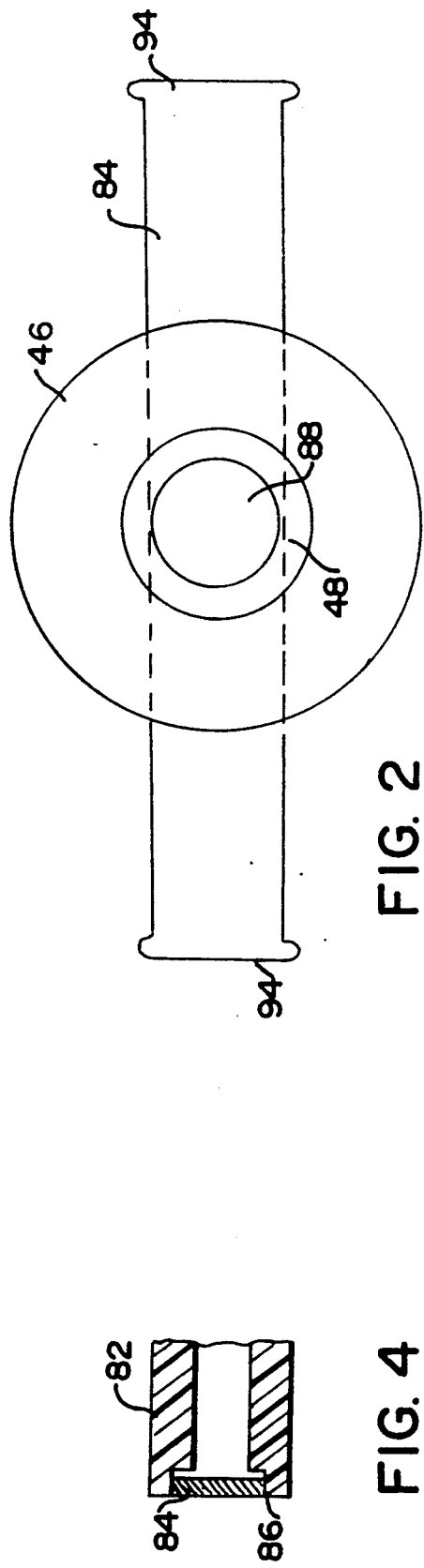
FIG. 1
FIG. 2
FIG. 4

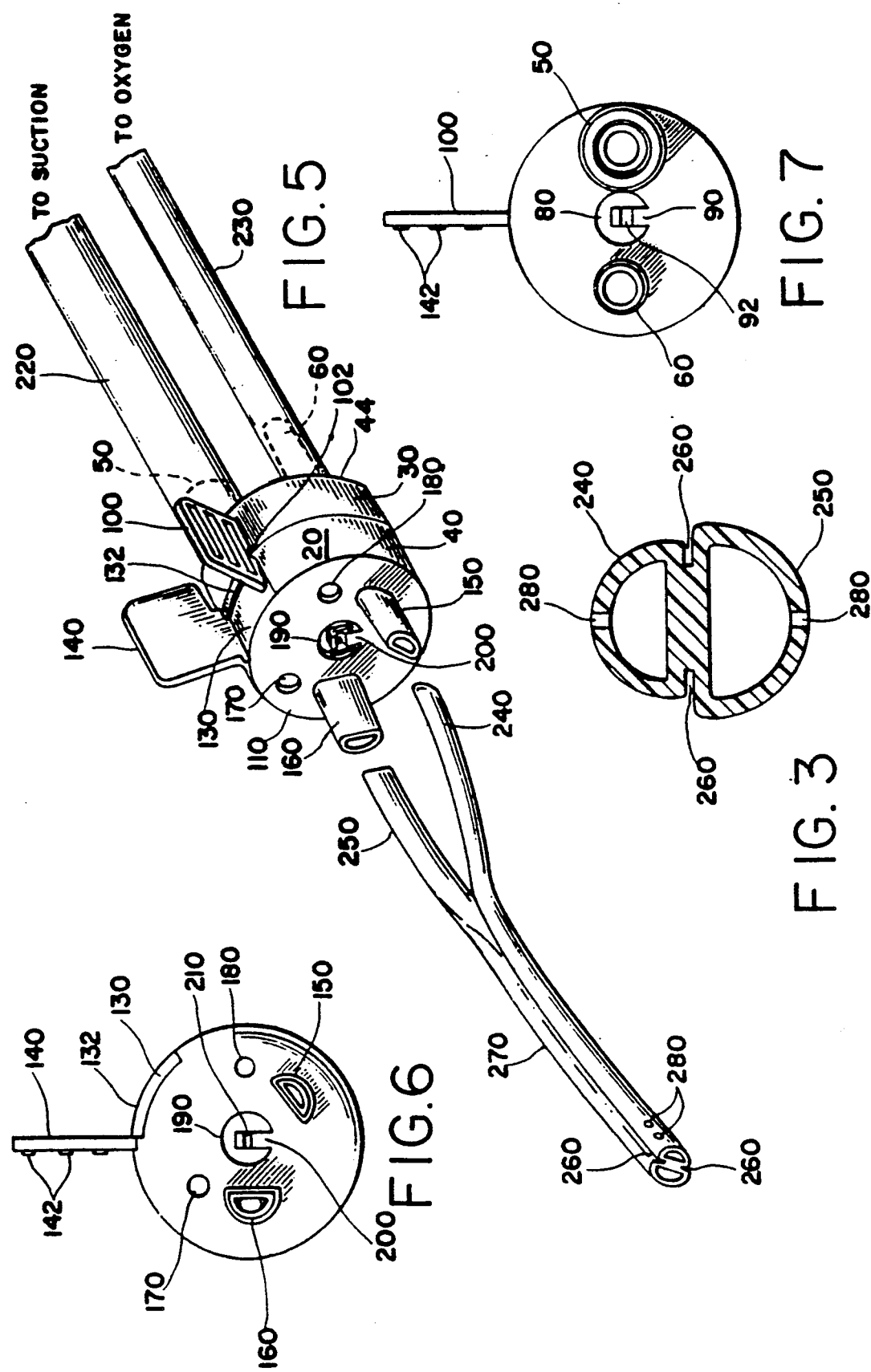

CLOSED SYSTEM REUSABLE DUAL PURPOSE CATHETER

BACKGROUND OF THE INVENTION

One type of system used for applying oxygen and suction to a patient, for example during or after surgery, uses a T shaped connector through which a catheter is introduced through the patient's mouth into the lungs.

In one known apparatus for performing the above-described operation using a catheter with a T connector, the catheter tube or lumen is fed through a sponge or the like into the T connector and then into the patient. The sponge is directly in one of the branches of the T connector and when the catheter is withdrawn through the sponge, mucus is trapped on the sponge in the passageway into the patient and thus can be drawn into the patient's lungs. This is a dangerous situation for the patient.

In addition, the prior art does not show a suctioning and oxygenating system which is a closed system which can prevent a patient from suffering oxygen depletion.

SUMMARY OF THE INVENTION

The above-described problems or failings in the prior art are solved by the present invention by means of a combination catheter and T connector wherein the sponge through which the catheter is drawn is not within the T connector but is in a chamber removed from the passageway and any mucus retained thereon cannot be drawn back into the patient. In addition, the system of the invention includes means which renders it a closed system which prevents a patient from suffering oxygen depletion during use.

DESCRIPTION OF THE DRAWINGS

FIG. 1 is a side elevational view of apparatus embodying the invention;

FIG. 2 is a sectional view along the lines 2—2 in FIG. 1;

FIG. 3 is a sectional view along the lines 3—3 in FIG. 1;

FIG. 4 is a sectional view along the lines 4—4 in FIG. 1;

FIG. 5 is a perspective view of the catheter and valve used in practicing the invention;

FIG. 6 is a front elevational view of the valve of FIGS. 1 and 5;

FIG. 7 is a rear elevational view of the valve of FIGS. 1 and 5;

DESCRIPTION OF THE INVENTION

Figure 8:
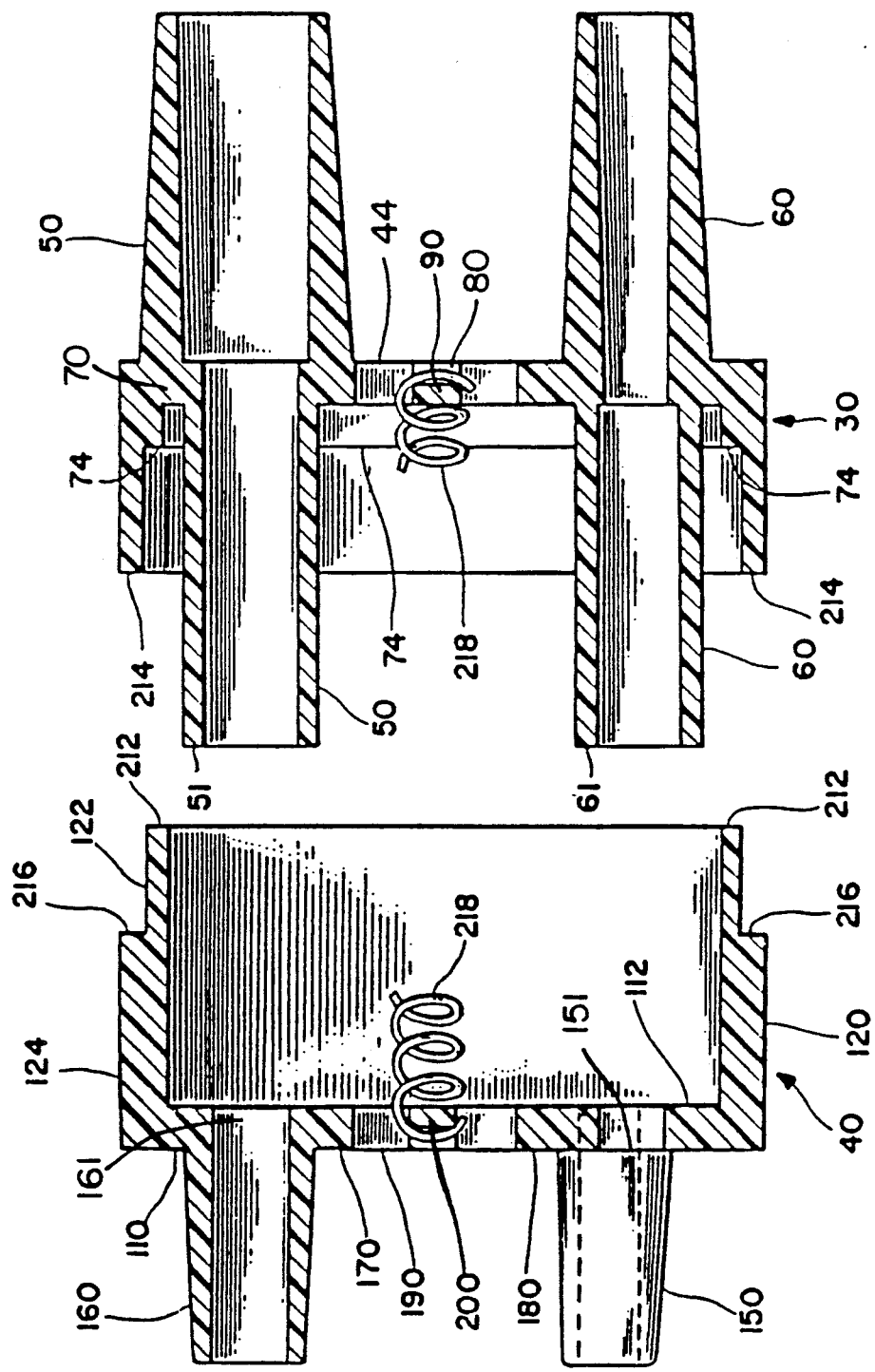
FIG. 8 is a sectional exploded view of the valve shown in FIGS. 1 and 5.
Figure 9:
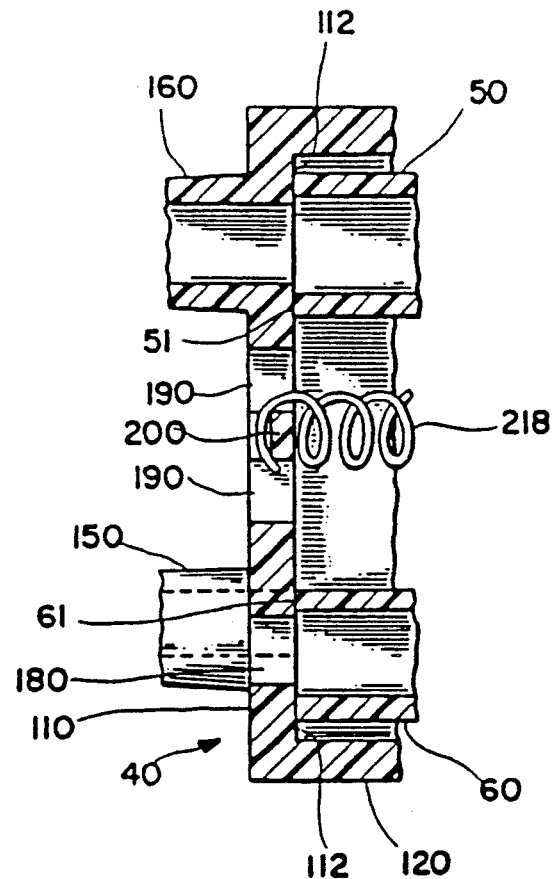
FIG. 9 is a side elevational view of a portion of the valve parts shown in FIG. 8 but assembled.

A catheter assembly 10 embodying the invention, referring to FIG. 1, includes a dual-purpose catheter assembly of the type described and claimed in U.S. Pat. No. 4,595,005 and incorporated herein by reference. The catheter assembly shown in the patent includes a double lumen unit 22, having flexible plastic tubes or lumen 240 and 250 secured together for most of their lengths, one being used to supply oxygen and one being used to provide suction. The flexible lumen tubes preferably have different diameters and shapes to insure proper connections to associated apparatus and in one form they have a cross-section as shown in FIG. 3.

The patient end 242 of the suction tube 250 is open and may have auxiliary holes not shown. The oxygen tube 240 may be open at its patient end and also includes auxiliary holes 280 along its patient end.

The lumen tubes 240 and 250 are connected at one end to a valve 20 for permitting the application of oxygen and suction to a patient as described in the above-identified patent.

It is understood that other catheter assemblies may be used in practising the present invention and this will be appreciated by those skilled in the art.

According to the invention, the catheter is used with a hollow, generally T shaped connector 24 which is a tubular member, preferably of plastic, having a cross member 26 (shown oriented horizontally in FIG. 1) which represents the cross-bar of the T and has a front or patient end 32 which is adapted to be placed in a patient's mouth. The other end or rear end 34 of the cross member carries within it a dry or wet sponge 36 of suitable size which is adapted to clean the end of the catheter lumen unit 22 as the lumen unit is withdrawn from a patient. The sponge 36 has a through-hole 38 through which the catheter lumen assembly 22 of flexible tubes 240 and 250 is pushed into the patient. Preferably, the hole 38 in the sponge matches the size and shape of the diameter of the catheter lumen unit as shown in FIG. 3.

A removable cap 42 is coupled to the rear end of the connector 24 to permit the sponge 36 to be removed and cleaned or replaced.

The T connector 24 also includes an arm 28 which extends downwardly from the cross portion and this arm is adapted to be coupled to a source of oxygen to be introduced into the patient. The arm 28 may or may not be at 90 degrees to the cross member 26 so that the connector 24 need not be exactly T shaped.

According to the invention, a wall 46 is provided in the cross member in the vicinity of the juncture of the arm 28 but on the side thereof closer to the rear end of the cross member and this wall 46 blocks the portion of the cross member behind it from the patient and the airway to the patient. The wall 46 has a generally central aperture 48.

A hollow tubular sleeve 82 is also provided in the rear portion of the connector 24. The sleeve 82, which may be of plastic, has its rear end bearing against the front end of the sponge 36 to hold the sponge in place and its front end bears against the rear surface of the wall 46. The sleeve 82 does not obstruct opening 48 in the wall 46.

Means is provided in the wall 46 for permitting the end 242 of the catheter lumen unit 22 to pass through and be directed into the patient. In addition, means is provided to block and unblock the opening 48 in the wall 46. This means, in one embodiment shown in FIGS. 1 and 2, includes a solid slide plate 84 seated behind the wall 46 in the rear portion or rear chamber of the connector 24 and slidable in guides formed on the rear surface of the wall 46 or in guide depressions 86 formed in the front end of the sleeve 82 as seen in FIG. 4. The slide plate 84 includes an aperture 88 and it extends through the wall of the connector to provide external portions 94 by means of which the slide can be manipulated so that its aperture 88 can be aligned with the aperture 48 in the wall 46 or it can be manipulated so that the solid portion of the slide blocks the opening 48. With the opening 88 in the slide plate 84 aligned with the opening 48 in the wall 46, the catheter lumen unit 22 can pass through the aligned openings into the front portion of the T connector and into the patient.

The plate 84 may also be mounted to rotate to achieve the desired blocking and unblocking of aperture 48.

An accordion sleeve or covering 96 is provided coupled to the rear end of the cross arm 26 of the connector 24 and enclosing the length of the catheter lumen unit 22 with its rear end connected to the valve 20 or to associated apparatus. The sleeve 96 includes a plurality of vent holes 98. The covering 96 provides a protective enclosure and may take any suitable form other than accordion.

In using the apparatus of the invention, the front or patient end of the T connector 24 is placed in the patient's mouth and the catheter lumen unit 22 is pushed through the sponge 36 into the aligned openings 48 and 88 in the wall 46 and slide plate 84, respectively, and through the remainder of the cross member 26 and into the patient. During this time, oxygen is fed through arm 28 and the front portion of the connector 24 into the patient. After the required procedure of oxygenating and suctioning the patient has been performed, the catheter is withdrawn and it proceeds through the opening 48 in the wall 46 without any mucus which may be on it being deposited on the wall 46. The opening 48 is closed by suitably sliding the slide plate 84 and then as the catheter passes through the sponge 36, it is cleaned of mucus and other matter. Since, the mucus, if any, is located in a closed compartment of the connector 24 which is sealed off from the patient by wall 46, there is no way by which mucus can be drawn back into the patient.

It is noted that some of the vent holes 280 at the patient end of the oxygen tube 240 lie outside the T connector and within the sleeve 96 for venting oxygen not fed to patient.

According to the invention, in order to render the apparatus described above a closed system in which the patient cannot lose oxygen when a suction operation is being performed, the catheter lumen unit is used with a valve mechanism 20 which is similar to that shown in the above-identified patent but embodies novel features not shown in the patent.

The valve 20 comprises two cylindrical bodies 30 and 40 having circular cross-sections and rotatably coupled together. One body 30 includes a flat rear wall 44 through which first and second integral tubes 50 and 60 extend so that the two tubes lie inside amd outside the body and thus inside the valve 20 when it is assembled. The inner ends 51 and 61 of tubes 50 and 60 are as smooth as possible for a purpose to be described. Tube 50 is used for connection to a suction source and tube 60 for connection to an oxygen supply, and the suction tube 50 is preferably of larger diameter. A portion 70 of the inner wall of the body 30 (FIG. 8) near rear wall 44 is thickened or is of reduced inside diameter to provide an annular ledge 74 which acts as a stop for the leading end of body 40 when the two are assembled. The rear wall 44 of the body 30 also has a central hole 80 and a notched tab 90 which is formed integral with the body 30 and extends partly across the hole 80. The tab 90 has a notch or depression 92 across its outer surface.

An operating finger tab 100 extends generally perpendicularly from the outer surface of the body 30 for manipulation by the operator of the catheter. The lower edge of tab 100 has a notch 102 for a purpose to be described.

The second body 40 includes a rear wall 110, whose inner surface 112 is as smooth as possible, for a purpose to be described. The annular outer wall 120 of body 40 has a portion 122 of reduced thickness or smaller outside diameter at its leading end for insertion into body 30. Also, the outer surface of the thicker portion 124 is provided with a region 130 of reduced thickness (FIG. 5) having a ledge 132 (FIGS. 5 and 6) where it joins the portion 122 of reduced thickness. An integral operating finger tab 140 extends generally perpendicularly from the thicker annular wall portion at one end of the portion 130 of reduced thickness.

The finger tabs 100 and 140 are provided with roughened strips 142 on their outer opposite faces, shown only in FIGS. 5, 6, and 7, to facilitate their manipulation by the user of the catheter.

Two tubes 150 and 160 extend away from the wall 110, one 150 for oxygen and one 160 for suction. The two tubes 150 and 160 communicate with the inside of the body 40 through holes 152 and 162 in the rear wall 110. The rear wall 110 also has two holes 170 and 180 located on the same circumference as the two tubes 150 and 160, and a central opening 190. A small integral tab 200 having a notch 210 extends part way across opening 190.

When the two bodies 30 and 40 are put together, the thin annular wall 122 of the body 40 fits snugly into the opening in body 30, and the leading end 212 butts up against the ledge 74. Similarly, the leading end 214 of body 30 butts up against ledge 216 where wall 122 meets wall 124 of the body 40. Also, the inner ends 51 and 61 of tubes 50 and 60 form a tight fit against the inner surface 112 of rear wall 110 of body 40 to provide an essentially leak-proof coupling between body 30 and body 40. When the bodies 30 and 40 are put together, the finger tab 100 slips over the rim 132, and the notch 102 in the lower surface thereof engages and locks in on the rim.

The two bodies 30 and 40 are held together securely and tightly by means of a helical spring 218 which is secured at its ends in the notches 92 and 210 in the tabs 90 and 200. In attaching the spring 218, with the two bodies 30 and 40 loosely coupled together, one end of the spring is shaped like a hook and is secured to notch 92, and, with the other end grasped by a hooked instrument, the spring is rotated to bias it, and then its other end, which is also shaped like a hook, is set in notch 210 in tab 200, and the bodies are locked together. The spring holds bodies 30 and 40 tightly together with the inner portions 51 and 61 of tubes 50 and 60 snug against the inner surface 112 of end wall 110. The bias set into the spring serves to keep the bodies 30 and 40 rotated so that the finger tabs 100 and 140 are at their maximum distance apart. With this orientation of the bodies, the oxygen tube 60 is aligned with the oxygen feed tube 150 through its hole 152 in wall 110, and the suction tube 50 is aligned with hole 170 and the ambient atmosphere. When the tabs 100 and 140 are squeezed together, the suction tube 50 is aligned with suction tube 160 through its hole 162 in the wall 110, and the oxygen tube 60 is aligned with the hole 180 and the ambient atmosphere.

The tube 50 is connected by flexible plastic tubing to a source of suction (not shown) and the tube 60 is similarly connected by tubing 230 to an oxygen source (not shown). The oxygen and suction tubes 150 and 160, on the patient side of the valve 20, are connected to the flexible tubes 240 and 250, rerspectively, which are coupled to the tubes 150 and 160. The oxygen tube 240 is of smaller diameter than the suction tube 250. The tubes 240 and 250 are manufactured as a single unit, and they preferably have generally semicircular cross-sections with the flat portions thereof adjacent to each other as seen in FIG. 3. Tubes 150 and 160 are similarly semicircular in cross section.

The tubes 240 and 250 are separated by a small amount at the valve ends to permit them to be handled and secured to the valve tubes 150 and 160. The unitary assembly of flexible tubes 240 and 250 is provided with well-defined grooves 260 between them as seen in FIGS. 1 and 6 and it is manufactured so that there is a natural curvature built into it.

When the catheter 10 is used, both the built-in curvature and the difference in the diameters of the tubes 240 and 250 combine to impart controllability of the assembly by the operator and it permits easy guidance of the patient ends of the tubes into the throat and lungs. In addition, as the tubes are moved and rotated, the grooves 261 act as a rake and loosen mucus which can be removed by suction.

To insure proper coupling of the oxygen tube 240 to the oxygen line of the valve 20 and the suction tube 250 to the suction line of the valve, the flexible tubes 240 and 250 are coupled to the valve 20 through an adapter 310 (FIG. 1) which is described and claimed in copending application Ser. No. 270,057 filed Nov. 14, 1988, now U.S. Pat. No. 4,995,387 which is incorporated herein by reference. The adapter 310 comprises a rigid plastic body having two through holes 320 and 330 and has front surface 340 and a rear surface 350. The holes 320 and 330 are shaped and dimensioned so that when the adapter is coupled to rigid tubes 150 and 160 on the patient side of the valve mechanism 20, hole 320 forms a tight fit with tube 160 and hole 330 forms a tight fit with tube 150.

In preferred normal use of the valve 20, the finger tabs 100 and 140 are apart and all of the associated parts are arranged so that oxygen flows from the oxygen source, through tube 230, valve tubes 60 and 150 and lumen tube 240 and into the patient. At the same time, the suction source is coupled through tube 50 to the valve hole 170 to the atmosphere. After oxygen has been administered for a desired period of time, the tabs 100 and 140 are pressed together to align the suction tubes 50 and 160 to flexible tube 250 so that suction is administered and the oxygen source is connected to valve hole 180 to the atmosphere. After a time, the finger tabs 100 and 140 are released and suction is discontinued and oxygen is applied again.

According to the invention, in order to render the system a closed system wherein the patient can be isolated from the valve 20 and cannot lose oxygen through the tubes 240 and 250. Valve 20 is constructed so that the entrance openings inside the valve to rigid tubes 150 and 160 and their attached flexible tubes 240 and 250 are alternately blocked off from the patient as suction and oxygen are applied to the patient.

Figure 10:
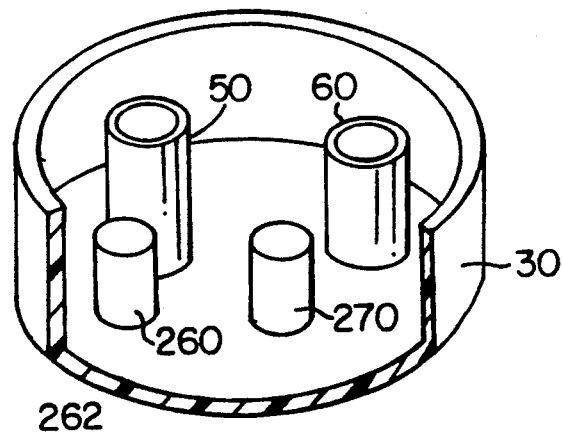
FIG. 10 is a perspective view of a modification of the valve of the invention.

According to the invention, refering to FIG. 10, this is achieved by providing a first solid boss or cylinder 260 on the inner surface 262 of the wall of valve portion 30 and positioned just beneath the tube 60. A similar second solid boss or cylinder 270 is provided on the surface 262 just beneath the tube 50. The two bosses are of such a length, like tubes 50 and 60, that they contact and form a tight fit against the inner surface 112 of valve portion 40 when the two parts 30 and 40 of the valve 20 are assembled. The bosses 260 and 270 are positioned so that, when the source of oxygen is connected through tube 60, tube 150 and tube 240 to the patient and the suction tube is coupled to the opening to the atmosphere, boss 260 blocks the opening to tube 160 and to the lumen 250 to the patient so that the patient cannot breathe into the valve through this lumen.

Similarly, when the suction lines are aligned and the patient is being suctioned, the source of oxygen is aligned with the opening to the atmosphere and the second boss 270 blocks the opening into tube 150 and to the oxygen lumen 240 to the patient. Thus the patient cannot breathe into or from the valve 20 through the oxygen lumen.

Thus, the bosses 260 and 270 operate to provide a closed system as far as the patient is concerned and the lumens 240 and 250 to the patient are alternately blocked from the valve 20 as the patient is alternately oxygenated and suctioned. This prevents the patient's lungs from losing oxygen through the valve 20.

Thus, in using the apparatus of FIG. 1 with the valve 20 containing the bosses 260 and 270, with oxygen flowing into the patient through the coupling member 24 when the tubes 240 and 250 are introduced into the patient and oxygen is administered, the volume of oxygen in the patient's lungs is increased over a base level. Then when suction is applied for a short period of time as required, although some oxygen may be sucked out, the level remains at about the safe base level. In addition, when suction is applied, since the oxygen line through the valve is blocked by a boss, oxygen cannot escape from the lungs through the valve. Sinmilarly, when oxygen is applied, the suction tube 250 is blocked by its boss in the valve and oxygen cannot be lost by the patient through the tube 250 and valve 20.

In order to prevent the catheter assembly from being withdrawn entirely from the T-connector 24 as it is being withdrawn from a patient, a flexible cord 282 is secured between the rear end 34 of connector 24 and the adapter 310. The cord 282 permits the catheter assembly to be inserted into the patient but when the assembly is withdrawn, it limits the extent to which it can be withdrawn and thus prevents it from being removed from the connector 24.

What is claimed is:

1. A dual-purpose apparatus for a pulmonary catheter comprising
    a rigid valve mechanism including a patient end and a second end for applying oxygen and suction thereto,
    a suction tube connected to said second end of said valve mechanism for applying suction thereto,
    an oxygen tube connected to said second end of said valve mechanism for applying oxygen thereto,
    a patient oxygen tube coupled to said patient end of said valve mechanism,
    a patient suction tube coupled to said patient end of said valve mechanism,
    said patient oxygen tube and said patient suction tube being adapted to have tubes coupled thereto for insertion into a patient,
    an oxygen vent hole and a suction vent hole in said valve mechanism,
    a first blocking means in said valve mechanism,
    a second blocking means in said valve mechanism, and means for moving said second end of said valve mechanism with respect to said patient end thereof whereby:

(1) when said suction tube is coupled to said patient suction tube to apply suction to a patient, said oxygen tube is not coupled to said patient oxygen tube, said oxygen vent hole and said suction vent hole being open, and said first blocking means obstructs said patient oxygen tube which is thereby blocked from communication with a patient, (2) when said oxygen tube is coupled to said patient oxygen tube said suction tube is not coupled to said patient suction tube, said suction vent hole and said oxygen vent hole being open and said second blocking means obstructs said patient suction tube which is thereby blocked from communication with a patient.

2. The apparatus defined in claim 1 wherein said first and second blocking means comprise solid bosses disposed inside said valve mechanism, one adjacent to said suction tube and one adjacent to said oxygen tube.

3. The apparatus defined in claim 2 wherein said bosses are solid tubular members.

4. The apparatus defined in claim 1 wherein said valve mechanism, said oxygen tube, said suction tube, said patient oxygen tube and said patient suction oxygen tube are of a rigid synthetic resinous material.

5. The apparatus defined in claim 1 wherein said valve mechanism comprises first and second cylindrical members coupled together for rotation with respect to each other.

6. The apparatus defined in claim 5 wherein said first cylindrical member includes a wall, having an inner surface and an outer surface, to which said suction tube and said oxygen tube are secured and said second cylindrical member includes a wall, having an inner surface and an outer surface, to which said patient suction tube and said patient oxygen tube are secured.

7. The apparatus defined in claim 6 wherein said suction tube and said oxygen tube extend from said wall of said first cylindrical member up to the inner surface of said wall of said second cylindrical member whereby said oxygen tube can be aligned with said patient oxygen tube and form a generally tight fit therewith and said suction tube can alternately be aligned with said patient suction tube and form a generally tight fit therewith.

8. The apparatus defined in claim 7 and including finger tabs secured to said first and second cylindrical members for rotating said first and second tubular members with respect to each other.

9. The apparatus defined in claim 7 wherein said bosses are secured to the inner surface of the wall of said first cylindrical member and they extend toward the inner surface of said wall of said second cylindrical member.

10. The apparatus defined in claim 1 and including flexible tube means coupled to said patient oxygen tube and said patient suction tube for insertion into a patient.

11. The apparatus defined in claim 10 and including a separate coupling member coupling said flexible tube means to said patient oxygen tube and said patient suction tube.

12. A dual-purpose catheter comprising
a valve mechanism including a patient end and an outlet end and including
a first cylindrical body and a second cylindrical body adapted to be coupled together so that they can rotate with respect to each other, said first body including a first suction tube and a second oxygen tube which extend from inside the body to outside the body for connection outside the body, one to a source of suction and one to a source of oxygen, said second body including a rear wall having first and second holes which communicate with first and second tubes which extend away from the outer surface of said rear wall for coupling to a patient for either suction or oxygen feed, the portions of said first and second tubes inside said first body being adapted to form a tight fit with said holes in said rear wall of said second body, a spring coupled at its ends to each of said bodies to hold said two bodies together, said spring being biased to hold said bodies rotated apart, finger operating means on said bodies for rotating said bodies to cause a selected alignment of either said suction tubes or said oxygen tubes, and first and second blocking members secured to said first cylindrical body inside said valve mechanism and positioned so that alternately, one blocks said first hole in said rear wall of said second body and one blocks said second hole in said rear wall of said second body.

13. A dual purpose catheter valve comprising
a valve body including a patient end an inlet end for suction and oxygen and including, a first cylindrical body and a second cylindrical body coupled together so that they can rotate with respect to each other, said first body including a suction tube and an oxygen tube which extend from inside the body to outside the body for connection outside the body, the suction tube being adapted to be connected to a source of suction and the oxygen tube being adapted to be connected to a source of oxygen, said second body including a wall having an inner surface and an outer surface, said wall having first and second holes one of which is for oxygen and the other of which is for suction, said first and second holes communicating with first and second tubes which extend away from the outer surface of said wall for coupling to a patient for either suction or oxygen feed, the portions of said oxygen and suction tubes of said first body inside said first body being adapted to form a tight fit with said first and second holes in said wall of said second body and with said inner surface of said wall of said second body, said oxygen and suction tubes extending up to and forming a tight fit with said rear surface of said wall, said wall of said second body also including two auxiliary holes which communicate with the atmosphere, the parts of said valve body being so arranged that, in operation thereof one of said tubes forms a tight fit with said wall in alignment with one of said holes to couple either suction or oxygen to a patient through said one of said holes, the tube which is not aligned with the other of said holes being aligned with one of said auxiliary holes, first and second blocking means in said valve mechanism positioned so that when one of said tubes couples suction to a patient, the hole which couples oxygen to a patient is blocked by said first blocking means and when the other of said tubes couples oxygen to a patient, the hole which couples suction to a patient is blocked by said second blocking means, and means securing together said first and second bodies.

14. The apparatus defined in claim 13 wherein said last named means comprises a spring coupled at its ends to each of said bodies to hold said two bodies together, and finger operated means on said bodies for rotating said bodies to cause a selected alignment of either said suction tube with its hole or said oxygen tube with its hole.

15. The apparatus defined in claim 13 wherein said blocking means comprises two solid tubes lying inside said first body and extending to the inner surface of said wall of said second body.

16. The apparatus defined in claim 13 and including flexible tube means coupled to said first and second tubes of said second body for insertion into a patient.

17. The apparatus defined in claim 16 and including a separate coupling member coupling said flexible tube means to said first and second tubes of said second body.

18. A dual purpose catheter comprising a valve mechanism having a patient end and an inlet end for coupling oxygen and suction thereto, a suction tube connected to the inlet end of said valve mechanism, an oxygen tube connected to the inlet end of said valve mechanism, and a unitary, two-part tube including a first tube and a second tube connected to the patient end of said valve mechanism, said first and second tubes having free ends to be inserted into a patient, one for feeding oxygen and one for suction, said first and second tubes being secured together along the greater portion of their lengths beginning at their free ends, said valve mechanism including first and second rotatable members coupled together and rotatable with respect to each other, said first member including a wall on the patient side of said valve mechanism, said wall having a suction hole and an oxygen hole with said suction tube being secured to the outer surface of said wall in alignment with said suction hole and said oxygen tube being secured to the outer surface of said wall in alignment with said oxygen hole, said second member including (1) an external suction tube for connection to a source of suction and an external oxygen tube for connection to a source of oxygen, (2) an internal suction tube aligned with and communicating with said external suction tube and an internal oxygen tube aligned with and communicating with said internal oxygen tube, said internal suction tube and internal oxygen tube extending toward said wall of said first member and forming a tight fit with said wall, and (3) first and second solid blocking posts positioned adjacent to said internal suction tube and internal oxygen tube and extending toward said wall of said first member and forming a tight fit therewith, the parts being arranged so that, as said first and second members are rotated with respect to each other, in one orientation said internal oxygen tube is aligned with said oxygen hole and feeds oxygen to a patient and said first blocking post blocks said suction hole to said patient and in a second orientation said internal suction tube is aligned with said suction hole and feeds suction to a patient and said second blocking post blocks said oxygen hole to the patient, the internal tube which is not aligned with its hole being aligned with one of said auxiliary holes.

19. The catheter defined in claim 18 wherein said valve mechanim is a rigid plastic body, first and second rigid short hollow tubes are secured to the outer surface of said wall of said first member, said first rigid tube being aligned with the suction hole in said wall and said second rigid tube being aligned with said oxygen hole in said wall.

20. The catheter defined in claim 19 wherein said first and second patient tubes of said unitary two-part tube assembly have a non-circular cross section and said first and second short rigid tubes have similar non-circular cross sections so that the two-part tube assembly can be properly coupled to said first and second rigid tubes.

* * * * *